(12) United States Patent
Chung

(10) Patent No.: US 11,230,423 B2
(45) Date of Patent: Jan. 25, 2022

(54) ABSORBING MEMBER STORING APPARATUS

(71) Applicant: QNQPHARM CO., LTD., Sejong (KR)

(72) Inventor: Woon Jin Chung, Seoul (KR)

(73) Assignee: QNQPHARM CO., LTD., Sejong (KR)

( * ) Notice: Subject to any disclaimer, the term of this patent is extended or adjusted under 35 U.S.C. 154(b) by 123 days.

(21) Appl. No.: 16/481,844

(22) PCT Filed: Apr. 4, 2018

(86) PCT No.: PCT/KR2018/003960
§ 371 (c)(1),
(2) Date: Jul. 30, 2019

(87) PCT Pub. No.: WO2018/190561
PCT Pub. Date: Oct. 18, 2018

(65) Prior Publication Data
US 2020/0062485 A1    Feb. 27, 2020

(30) Foreign Application Priority Data

Apr. 12, 2017 (KR) .......................... 10-2017-0047603

(51) Int. Cl.
*B65D 81/32* (2006.01)
*A61L 2/20* (2006.01)

(52) U.S. Cl.
CPC ............ *B65D 81/3222* (2013.01); *A61L 2/20* (2013.01); *A61L 2202/23* (2013.01); *A61L 2202/24* (2013.01)

(58) Field of Classification Search
CPC ................... B65D 81/3222; B65D 81/3216; B65D 81/32; B65D 81/3238
(Continued)

(56) References Cited

U.S. PATENT DOCUMENTS 1,706,335 A * 3/1929 Toch ....................... B44D 3/122
220/506
4,410,085 A * 10/1983 Beneziat ............ B65D 81/3216
206/217
(Continued)

FOREIGN PATENT DOCUMENTS

JP     S56-053443 U    5/1981
JP     H11-299902 A   11/1999
(Continued)

*Primary Examiner* — Steven A. Reynolds
(74) *Attorney, Agent, or Firm* — Korus Patent, LLC; Seong Il Jeong

(57) ABSTRACT

The present invention relates to an absorbing member storing apparatus, and includes a first storing part (110) in which an absorbing member is stored, a second storing part (120), and a fastening part (130). The fastening part (130) is formed inside the first storing part (110), and the second storing part is fitted into the fastening part (130). According to the present invention, through the opening of the storing apparatus in which an absorbing member and a fluid have been separately stored, the absorbing member, such as sterilized cotton, a sterilized cotton swab, or the like, can be immediately wet with the fluid, thereby enabling the significantly hygienic and convenient storage and use of an absorbing member.

6 Claims, 6 Drawing Sheets

(58) Field of Classification Search
USPC .................... 206/205, 209, 210, 219, 221
See application file for complete search history.

(56) References Cited

U.S. PATENT DOCUMENTS

| | | | | |
|---|---|---|---|---|
| 4,720,351 | A | * | 1/1988 | Flynn .................. B65D 51/28 |
| | | | | 206/568 |
| 5,378,226 | A | * | 1/1995 | Hanifl ................ A61M 35/006 |
| | | | | 206/438 |
| 8,083,056 | B1 | * | 12/2011 | Wu .................. B65D 81/3222 |
| | | | | 206/221 |
| 2009/0211927 | A1 | * | 8/2009 | Wu .................. B65D 81/3222 |
| | | | | 206/219 |

FOREIGN PATENT DOCUMENTS

| | | |
|---|---|---|
| KR | 10-0869317 B1 | 11/2008 |
| KR | 10-2009-0034471 A | 4/2009 |
| KR | 10-2014-0020140 A | 2/2014 |

* cited by examiner

ABSORBING MEMBER STORING APPARATUS

TECHNICAL FIELD

The present invention relates to an absorbing member storing apparatus, and more specifically to an absorbent hygiene article storing apparatus which enables an absorbent hygiene article, such as cotton, a cotton swab, gauze, or a sponge, to be hygienically stored and used.

BACKGROUND ART

Absorbing members, such as towels, cotton, and cotton swabs, are mainly wet with a fluid, such as water, or a disinfection fluid, and are then used. For example, when a cotton swab or cotton is used, it is wet with a disinfection fluid or the like and then used rather than being used alone.

As described above, there are many cases where absorbing members and a fluid are used together. Accordingly, there may be considered a method of wetting absorbing members with a fluid in advance and then distributing the absorbing members wet with the fluid. However, when absorbing members are distributed in a wet state, even completely sterilized absorbing members continue to be wet with the fluid until use, and thus there is greater concern about contamination and bacterial infection.

Meanwhile, when absorbing members and a fluid are provided in separate storing devices, the above-described problem does not occur. However, when an absorbing member and a fluid are used together, as in a case where a disinfection fluid is applied to gauze or the like and then used, inconvenience occurs in that a user must separately find the absorbing member and the fluid. Furthermore, there are many cases where any one of the absorbing members and the fluid provided in the separate storing devices is exhausted first. Accordingly, it is difficult to hygienically manage the remaining absorbing members or fluid, and burdensomeness occurs in that a user needs to separately purchase the remaining absorbing members or fluid.

Korean Utility Model Registration No. 0273040 discloses an apparatus in which a case for storing cotton swabs, which are a type of absorbing members, is combined with a liquid medicine container. However, they are carried together by a coupling device, but cannot be stored in a compact manner in almost the same manner as they are contained in existing separate containers. Furthermore, absorbing members, such as cotton swabs, and cotton, are frequently used in skin, wound mucous membranes, and the like in medical institutions, and it is crucial to maintain a sterilized state. Korean Utility Model Registration No. 0273040 has a problem in that the disadvantage in which when an absorbing member is a sterilized product, a sterilized state must be maintained until use is not overcome.

DISCLOSURE

Technical Problem

An object of the present invention is to provide an absorbing member storing apparatus which can reduce the risk of bacterial growth even when an absorbing member is stored for a long time and which facilitates use and storage.

Furthermore, the present invention enables the processes of processing an absorbing member and a fluid, having different handling methods regarding the performance of sterilization or the like, to be separately performed and also enables the processed absorbing member and fluid to be combined into a single absorbing member storing apparatus, thereby enabling the significantly hygienic and efficient process of manufacturing an absorbing member storing apparatus.

Furthermore, an object of the present invention is to provide an absorbing member storing apparatus which enables an absorbing member to be used immediately after a fluid has been easily absorbed into an absorbing member and which can reduce the inconvenience in which the fluid and the absorbing member need to be separately stored.

Furthermore, an object of the present invention is to provide an absorbing member storing apparatus which the present invention which can minimize the degree of the contamination of an absorbing member by a fluid and the degree of the contamination of the fluid by the absorbing member, i.e., which can block cross contamination between the absorbing member and the fluid.

Furthermore, an object of the present invention is to provide an absorbing member storing apparatus which is very economical and hygienic because the amount of fluid and the amount of absorbing member are equally exhausted.

Technical Solution

In order to accomplish the above objects, according to the present invention, there is provided an absorbing member storing apparatus, including:

a first storing part in which an absorbing member is stored; a fastening part which is provided on the inner bottom surface of the first storing part; and a second storing part which is formed as a tube having an open top and bottom, which is fitted into the fastening part, and in which a fluid is stored. The second storing part in which the fluid is stored is configured to store the fluid without leakage and to, upon use, be separated from the fastening part and allow the fluid to flow into the first storing part and to be applied to the absorbing member. Meanwhile, the second storing part is formed as a tube having an open top and bottom. Accordingly, when the lower end of the second storing part is coupled to the fastening part, a space adapted to contain the fluid is provided. In contrast, when the second storing part is separated from the fastening part, the bottom of the second storing part has an open state, and thus the fluid is applied to the absorbing member in the first storing part.

The lid of the first storing part may be formed in a doughnut shape which covers the first storing part in which the absorbing member has been stored while covering the upper-end hole of the second storing part. Furthermore, the lid of the first storing part and the second storing part may be formed in an integrated manner by injection molding.

The lower end of the second storing part is screwed into the fastening part, and the lid of the first storing part is connected to the second storing part. Accordingly, by force applied to rotate or lift the lid of the first storing part, the lower end of the second storing part coupled to the fastening part is also separated from the fastening part.

In one embodiment, the lid of the first storing part further includes a hole which is capable of gas sterilizing the inside of the first storing part.

In one embodiment, the second storing part may have a bottle shape which has a narrowing upper end or lower end.

In one embodiment, the absorbing member is at least any one of cotton, a cotton swab, a towel, gauze, a nonwoven fabric, and sponge.

In one embodiment, the fluid is a disinfection fluid.

In one embodiment, the absorbing member storing apparatus further includes an overcap which can perform sealing after the fluid has been contained inside the second storing part.

In one embodiment, the fastening part further includes a blocking portion which prevents the absorbing member stored in the first storing part from moving to a center after the second storing part has been lifted up.

In one embodiment, the absorbing member storing apparatus further includes a partition portion which is formed upward from the inner bottom surface of the first storing part.

Advantageous Effects

The absorbing member storing apparatus according to the present invention is configured such that an absorbing member and a fluid are separately stored within a single apparatus and the stored fluid flows out and wets the absorbing member only when a user allows the absorbing member to be wet with the fluid and then uses the wet absorbing member by opening the storing apparatus, unlike the conventional invention, thereby enabling the hygienic storage of the absorbing member.

The present invention facilitates the use and storage of an absorbing member and a fluid because the absorbing member and the fluid do not need to be separately provided.

Furthermore, the absorbing member storing apparatus can be significantly efficiently manufactured because an absorbing member and a fluid are separately sterilized according to their characteristics and standards and are then combined.

Figure 1:
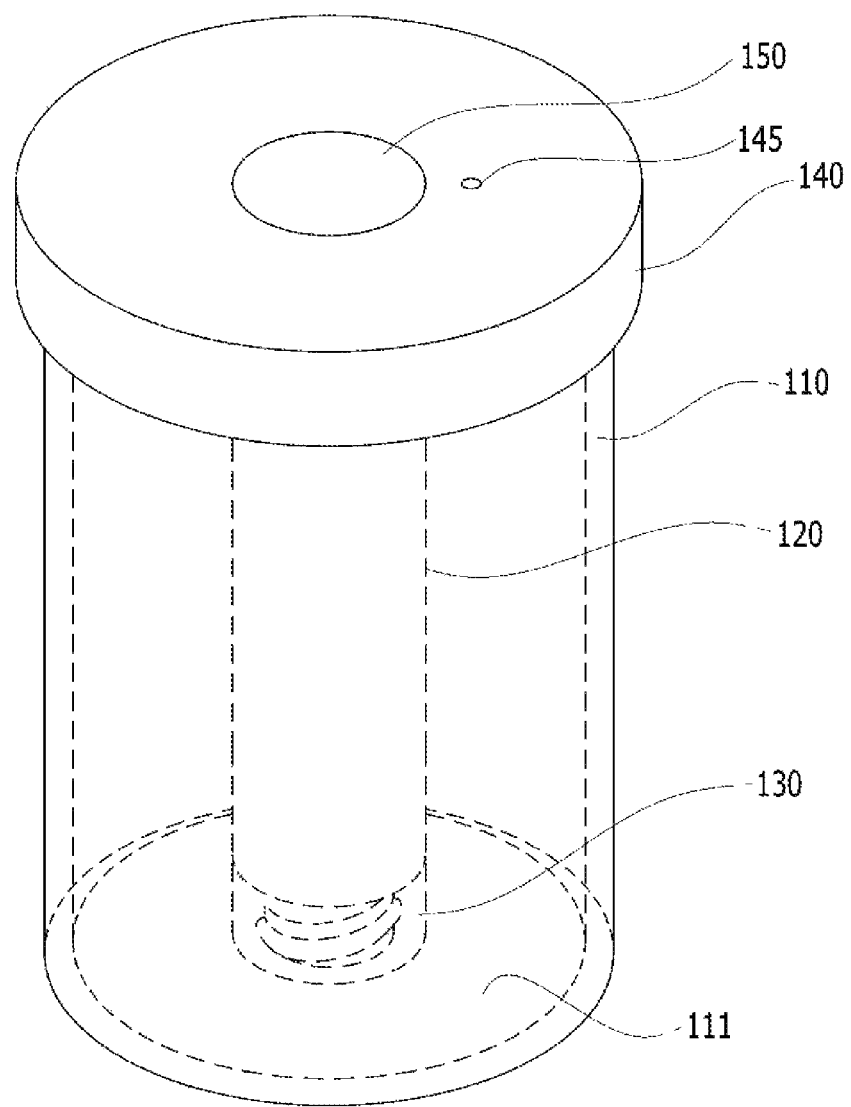
FIGS. 1 and 2 are perspective views showing an absorbing member storing apparatus according to a first embodiment of the present invention.
Figure 2:
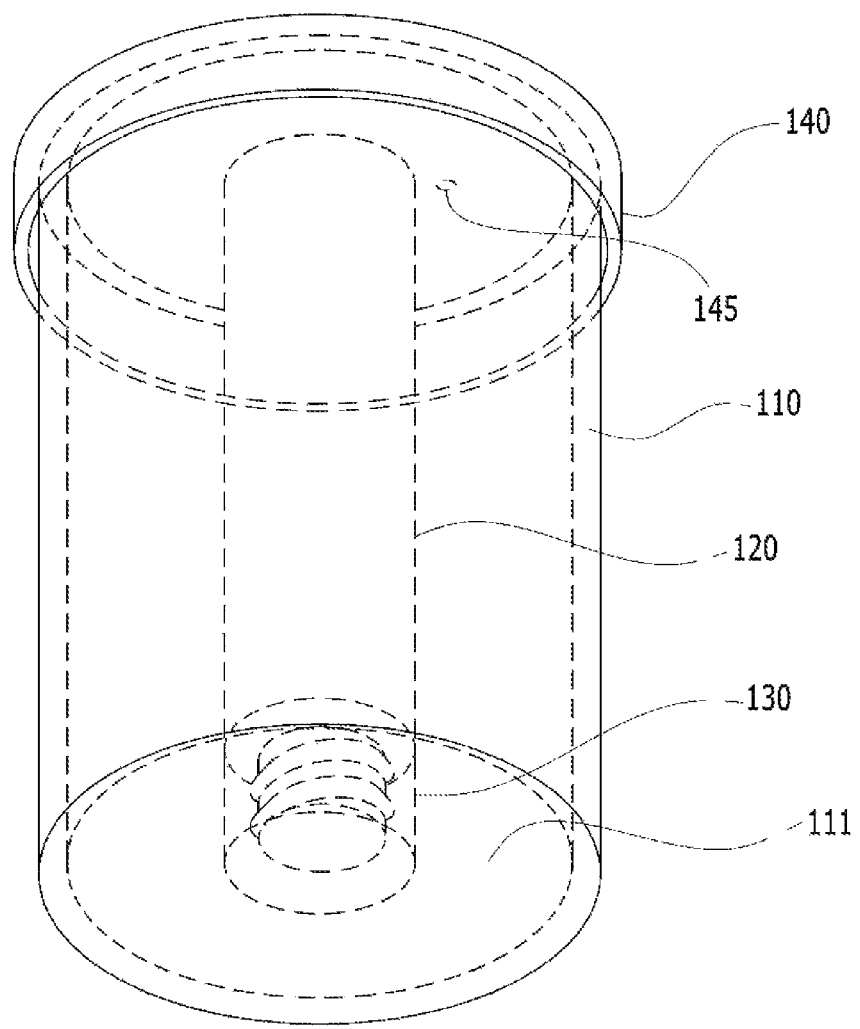

Descriptions of reference symbols are as follows:
110: first storing part
111: bottom surface of first storing part
120: second storing part
130: fastening part
131: connecting cap
135: blocking pin
140: lid of first storing part
145: gas hole
150: overcap

BEST MODE

Details of the present invention will be described in greater detail below with reference to the accompanying drawings. In this process, the thicknesses of lines and the sizes of components may be exaggerated for the sake of clarity and convenience. Furthermore, the following terms are defined by considering functions in the present invention, and the definitions thereof may be changed according to a user or operator's intention or practice. Therefore, the terms should be defined in the overall context of the specification.

An absorbing member storing apparatus according to a first aspect of the present invention includes a first storing part 110, a second storing part 120, and a fastening part 130, as shown in FIG. 1.

In greater detail, the first storing part 110 configured such that an absorbing member is stored therein and the second storing part 120 provided inside the first storing part are provided, and the fastening part 130 protrudes from the center of the bottom surface of the first storing part 110 in the ring-shape of a stop protrusion. The second storing part 120 is coupled into the fastening part 130.

Figure 3:
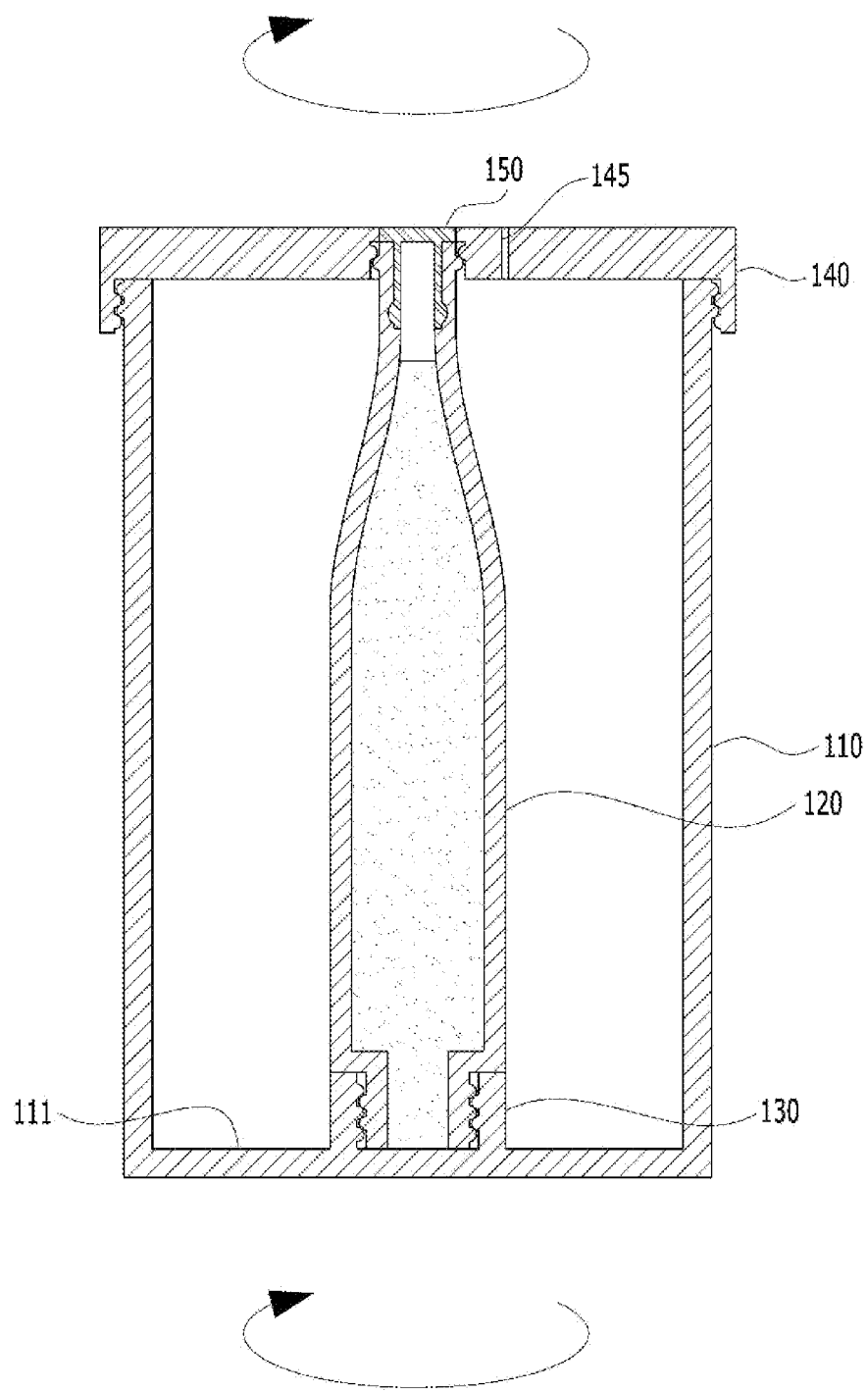
FIGS. 3-5 are sectional views showing the absorbing member storing apparatus according to the first embodiment of the present invention.
Figure 4:
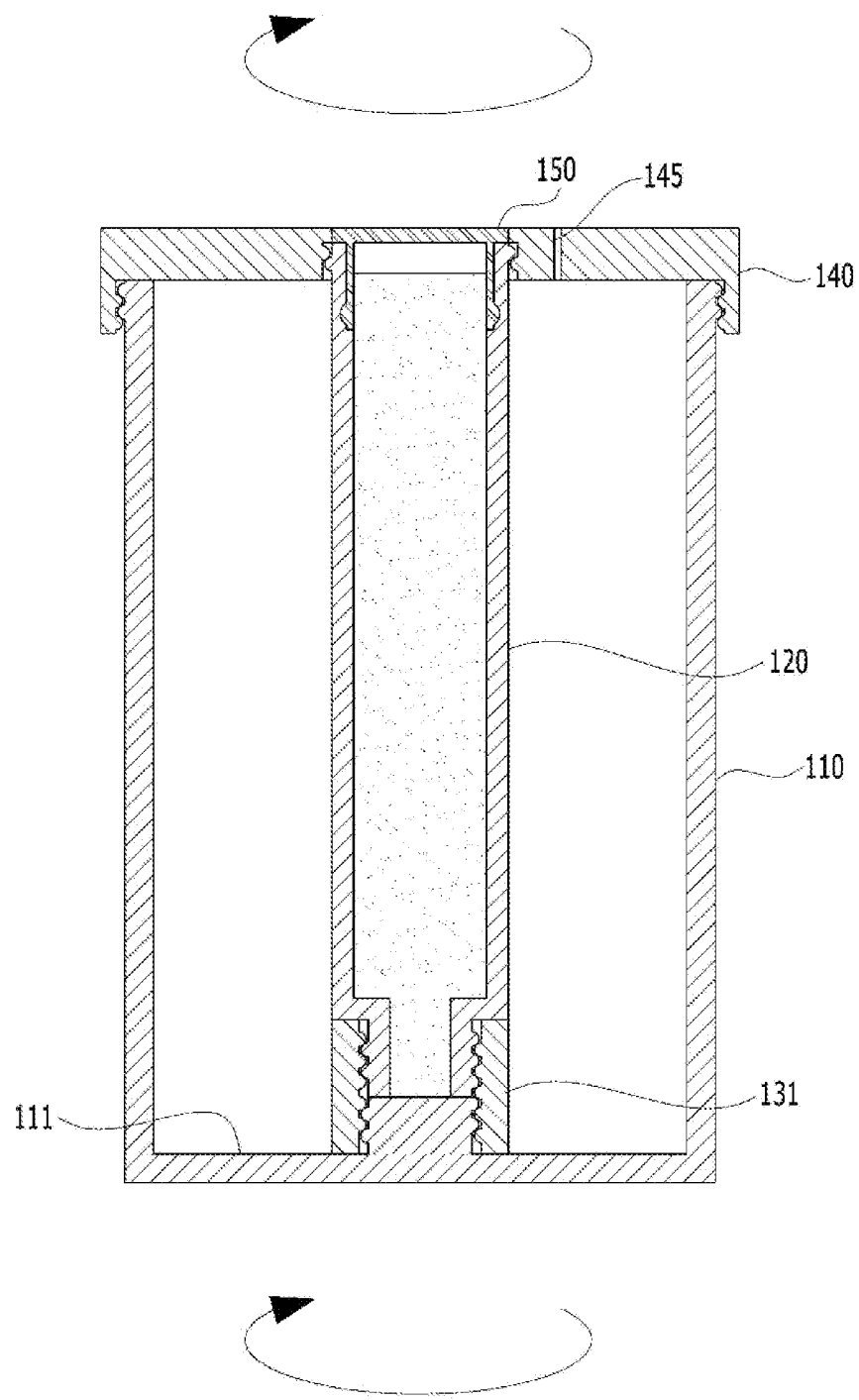

As shown in FIGS. 3 and 4, the second storing part 120 forms a tube of a shape having open top and bottom. As the lower end of the second storing part 120 is coupled to the fastening part 130, a bottom surface is formed, and thus a fluid flows into the hole of the upper end of the second storing part 120 and is then stored.

A fluid, such as water or a disinfection fluid, is stored inside the second storing part 120 formed as described above, and the flow of the fluid to the first storing part is blocked. The second storing part 120 has a cylindrical shape, as shown in FIG. 1 or a shape configured to form a space for storing a fluid, but the shape of the second storing part 120 is not limited. As shown in FIG. 3, the second storing part may be formed in a shape, such as a shape in which the upper end thereof is reduced or a shape in which the lower end thereof is reduced.

The second storing part 120 is formed in such a manner that the lid 140 of the first storing part is connected to the hole of the upper end of the second storing part. The second storing part 120 and the lid 140 of the first storing part may be formed in an integrated manner by injection molding.

When rotating force or upward external force is applied to the upper and lower ends of the second storing part 120 connected with the lid of the first storing part in an integrated manner by the force by which the lid 140 of the first storing part is opened, the second storing part 120 is separated from the fastening part 130 and moved upward, and thus the stored item is applied to the absorbing member.

The second storing part needs to be tightly fitted into the fastening part provided at the center of the bottom surface 111 of the first storing part 110 so that the fastening part 130 blocks the leakage of the fluid stored in the second storing part 120 except for a case where the second storing part 120 is moved upward by external force.

The fastening part 130 and the bottom surface of the first storing part 110 may be formed in an integrated manner by injection molding.

The lower end of the second storing part and the fastening part 130 may be screwed into each other so that the second storing part 120 can be stably fastened to the fastening part 130 without movement and can be then separated from the fastening part 130 by applying rotating force when a user uses the apparatus.

Furthermore, as shown in FIG. 4, in the fastening part 130, a protrusion is formed at the center of the bottom surface 111 of the first storing part 110, and the protrusion of the bottom surface 111 and the lower end of the second storing part 120 are fastened in a screw manner by the connecting cap 131.

Figure 5:
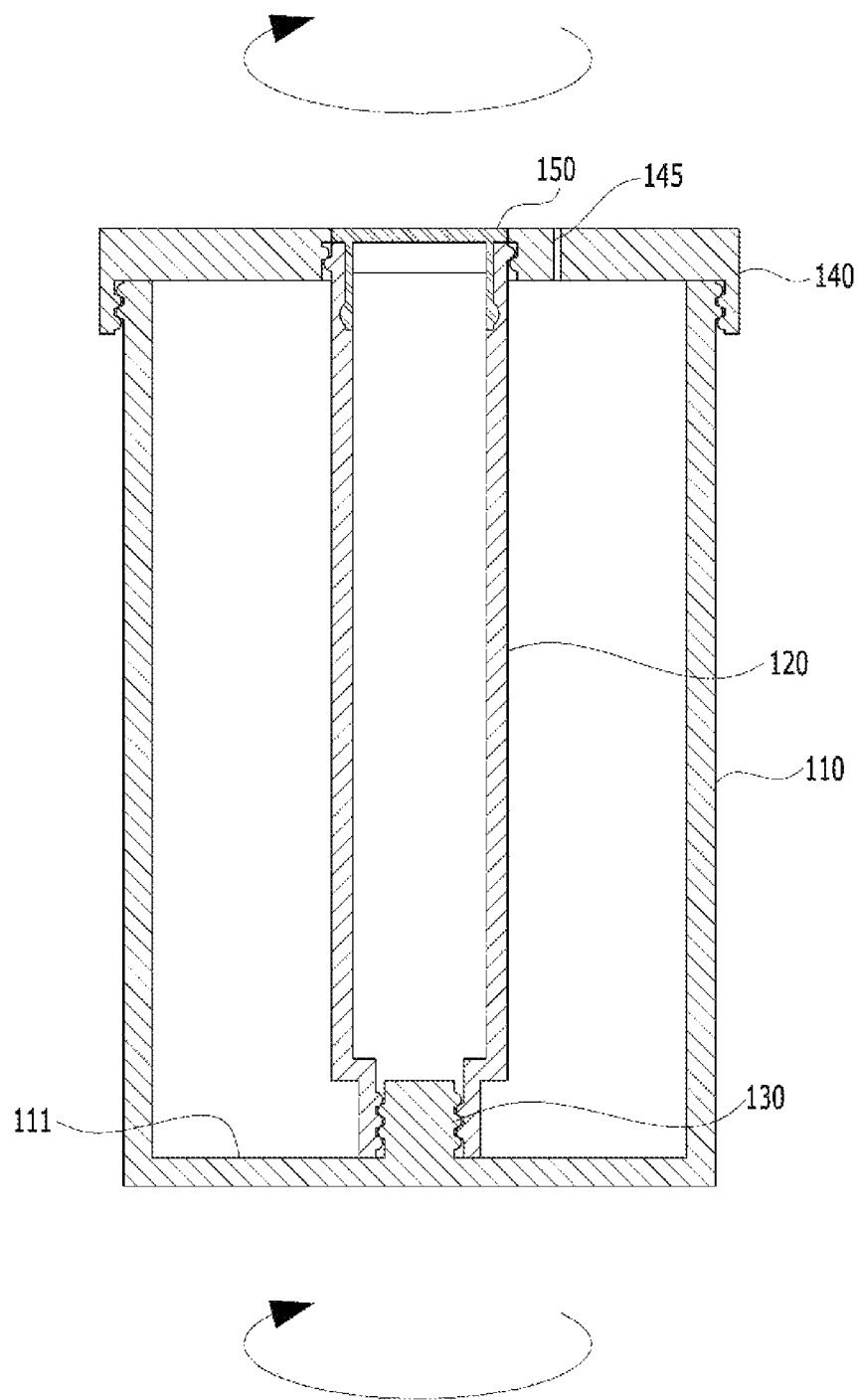
Figure 6:
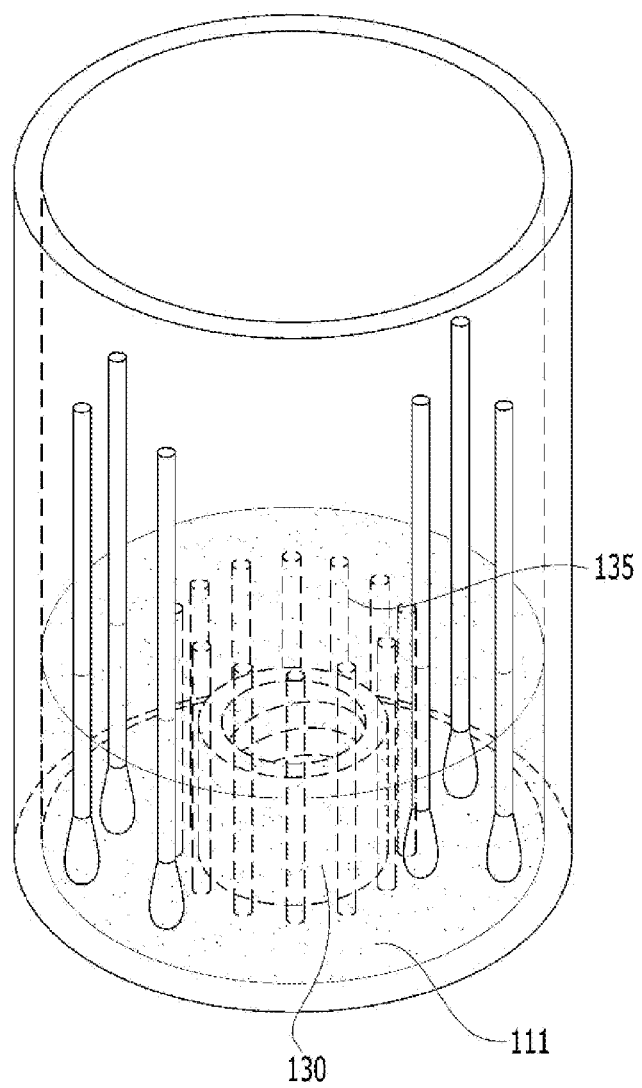
FIG. 6 is a perspective view showing a state that is obtained after the second storing part of the present invention has been lifted.

As shown in FIG. 5, blocking pins 135 may be formed around the fastening part 130 at predetermined intervals, and may prevent the absorbing member from moving in the direction of the center of the fastening part after the second storing part has been separated and lifted from the fastening part 130.

Although the present invention has been described with reference to the embodiments shown in the drawings, this is merely illustrative. Accordingly, it will be appreciated by a person having ordinary skill in the art to which the corresponding technology pertains that various modifications and other equivalent embodiments may be made from the foregoing description.

Therefore, the true technical scope of the present invention should be defined by the following claims.

MODE FOR INVENTION

As described above, the present invention is directed to an apparatus which enables an absorbing member and a fluid having different sterilization and disinfection processes to be efficiently combined and stored. Accordingly, the following description will be given based on the processes of storing and processing the absorbing member and the fluid according to the present apparatus.

First, as the first storing part 110 is filled with the absorbing member and the second storing part 120 integrated with the lid 140 of the first storing part is fitted into the fastening part 300, the first storing part is covered with the lid and, simultaneously, a space configured to accommodate the fluid is formed in the second storing part. After the fluid has been provided in the second storing part, the overcap 150 of the second storing part is seated. A gas hole 145 configured to disinfect the absorbing member with sterilizing gas is formed through the lid 140 of the first storing part integrated with the second storing part 120. After the sterilization of the absorbing member has been completed, the absorbing member and the fluid are stored in a compact manner through a very simple process.

When the absorbing member and fluid sterilized as described above are separately sealed and stored, they are provided in the first storing part and the second storing part, respectively, until they are used. When a user applies upward force or rotating force to the lid 140 of the first storing part integrated with the upper end 140 of the second storing part, the lid of the first storing part is opened and, simultaneously, the second storing part 120 is separated from the fastening part 130, thereby enabling the fluid stored in the second storing part to be easily applied to the absorbing member. In other words, a user enables the fluid to be automatically applied to the absorbing member without any extra effort at the start of use and, thus, can immediately use the absorbing member wet with the fluid.

INDUSTRIAL APPLICABILITY

The present absorbing member storing apparatus allows an absorbing member and a fluid to be separately sterilized according to their characteristics and standards and then to be combined, thereby enabling the considerably efficient manufacture of the absorbing member storing apparatus. Furthermore, a user stores the absorbing member and the fluid within the single apparatus and allows the absorbing member to be wet with the fluid by opening the storing apparatus when the absorbing member is used, thereby enabling the hygienic storage and use of the absorbing member.

The invention claimed is:

1. An absorbing member storing apparatus, comprising:
   a first storing part which has a cylindrical shape in which a lid is coupled to an upper end of the cylindrical shape, which includes a fastening part which protrudes from a bottom surface, and in which an absorbing member is stored;
   a second storing part which is formed as a tube having an open top and bottom, which is coupled to the first storing part inside the first storing part in such a manner that a lower end of the tube is fitted into the fastening part, and in which a fluid is stored; and
   an overcap configured to detachably and separately cover an upper end of the second storing part such that the upper end of the second storing part is sealed or unsealed, the overcap being separable from the lid,
   wherein the upper end of the second storing part is formed with the lid, covering the first storing part, in an integrated manner,
   wherein the second storing part remains coupled to the first storing part by the fastening part, and, upon opening attributable to use of the first storing part, the second storing part is separated from the fastening part and, simultaneously, the fluid inside the second storing part is applied to the absorbing member.

2. The absorbing member storing apparatus of claim 1, wherein the fastening part and the second storing part are coupled to each other by male and female threads.

3. The absorbing member storing apparatus of claim 1, wherein the fastening part forms a protrusion at a center of the bottom surface of the first storing part, and the protrusion and a lower end of the second storing part are coupled to each other by a connecting cap.

4. The absorbing member storing apparatus of claim 1, wherein a plurality of blocking portions is formed on an outer circumferential surface of the fastening part.

5. The absorbing member storing apparatus of claim 2, wherein a plurality of blocking portions is formed on an outer circumferential surface of the fastening part.

6. The absorbing member storing apparatus of claim 3, wherein a plurality of blocking portions is formed on an outer circumferential surface of the fastening part.

* * * * *